US00PP15924P2

(12) United States Plant Patent
Hill, Jr.

(10) Patent No.: US PP15,924 P2
(45) Date of Patent: Aug. 16, 2005

(54) *GUZMANIA* PLANT NAMED 'HOLIDAY'

(50) Latin Name: ***Guzmania* sp.**
Varietal Denomination: Holiday

(75) Inventor: Herbert H. Hill, Jr., Lithia, FL (US)

(73) Assignee: Twyford International, Inc., Santa Paula, CA (US)

( * ) Notice: Subject to any disclaimer, the term of this patent is extended or adjusted under 35 U.S.C. 154(b) by 14 days.

(21) Appl. No.: 10/955,479

(22) Filed: Sep. 30, 2004

(51) Int. Cl.[7] ..... A01H 5/00
(52) U.S. Cl. ..... Plt./371
(58) Field of Search ..... Plt./371

(56) References Cited

U.S. PATENT DOCUMENTS

PP8,221 P * 5/1993 Bak et al. ..... Plt./371
5,453,563 A * 9/1995 Bak et al. ..... 800/323
PP10,852 P * 4/1999 Bak et al. ..... Plt./371
PP12,176 P2 * 10/2001 Hill, Jr. ..... Plt./371

* cited by examiner

*Primary Examiner*—Anne Marie Grunberg
*Assistant Examiner*—W. C. Haas

(74) *Attorney, Agent, or Firm*—C. A. Whealy

(57) ABSTRACT

A new and distinct cultivar of *Guzmania* plant named 'Holiday', characterized by its compact, upright and outwardly arching plant habit; green-colored foliage with purple-colored striations towards the base; inflorescences held upright and above foliage on strong scapes; inflorescences with closely-spaced dark purple-colored flower bracts that are tipped with white; and long-lasting inflorescences that maintain good coloration for about two to three months.

2 Drawing Sheets

Botanical designation: *Guzmania* sp.
Variety denomination: 'Holiday'.

BACKGROUND OF THE INVENTION

The present Invention relates to a new and distinct cultivar of *Guzmania* plant, botanically known as *Guzmania* sp. and referred to by the cultivar name 'Holiday'.

*Guzmania* is native to tropical America. Leaves of the *Guzmania* are usually formed as basal rosettes which are stiff and arranged in several vertical ranks. *Guzmania* have terminal flower spikes of panicles which are often bracted with petals united in a tube about as long as the calyx.

The new *Guzmania* is a product of a planned breeding program conducted by the Inventor in Lithia, Fla. The objective of the breeding program is to create new *Guzmania* cultivars with a plant habit appropriate for container production, desirable flowering habit and inflorescence coloration and good postproduction longevity.

The new *Guzmania* originated from a cross-pollination made by the Inventor in Lithia, Fla. in March, 1996, of the *Guzmania* sp. cultivar Ultra (U.S. Plant Pat. No. 8,221 and U.S. Pat. No. 5,453,563), as the female, or seed, parent with the *Guzmania lingulata* cultivar El Cope, not patented, as the male, or pollen, parent. The cultivar Holiday was discovered and selected by the Inventor as a flowering plant within the progeny of the stated cross in a controlled environment in Lithia, Fla., in May, 1999.

Asexual reproduction of the new *Guzmania* by off-shoots in a controlled environment in Lithia, Fla. since Jul. 7, 1999, has shown that the unique features of this new *Guzmania* are stable and are reproduced true to type in successive generations. Asexual reproduction of the new *Guzmania* by tissue culture done in a laboratory in Sebring, Fla. since September, 1999, has also confirmed that the unique features of this new *Guzmania* are stable and are reproduced true to type in successive generations.

SUMMARY OF THE INVENTION

The new *Guzmania* has not been observed under all possible environmental conditions. The phenotype may vary somewhat with variations in environment such as temperature and light intensity without, however, any variance in genotype.

The following characteristics have been repeatedly observed and are determined to be basic characteristics of 'Holiday' and distinguish 'Holiday' as a new and distinct cultivar:

1. Compact, upright and outwardly arching plant habit.
2. Green-colored foliage with purple-colored striations towards the base.
3. Inflorescences held upright and above foliage on strong scapes.
4. Inflorescences with closely-spaced dark purple-colored flower bracts that are tipped with white.
5. Long-lasting inflorescences that maintain good coloration for about two to three months.

Plants of the new *Guzmania* can be compared to plants of the female parent, the cultivar Ultra. In side-by-side comparisons conducted in Lithia, Fla., plants of the new *Guzmania* differed from plants of the female parent in the following characteristics:

1. Plants of the new *Guzmania* were larger than plants of the female parent.
2. Plants of the new *Guzmania* and the female parent differed in foliage color.

3. Plants of the new *Guzmania* had larger and taller inflorescences than plants of the female parent.
4. Inflorescences of plants of the new *Guzmania* had many white-tipped terminal bracts whereas inflorescences of plants of the female parent had relatively few white-tipped terminal bracts.

Plants of the new *Guzmania* can be compared to plants of the male parent, the cultivar El Cope. In side-by-side comparisons conducted in Lithia, Fla., plants of the new *Guzmania* differed from plants of the male parent in the following characteristics:

1. Plants of the new *Guzmania* were smaller and more compact than plants of the male parent.
2. Plants of the new *Guzmania* grew more rapidly than plants of the male parent.
3. Plants of the new *Guzmania* had dark purple-colored flower bracts whereas plants of the male parent had bright red-colored flower bracts.

Of the other commercial *Guzmania* cultivars known to the Inventor, none compare well to the new *Guzmania* due to its unique combination of leaf and flower bract coloration.

BRIEF DESCRIPTION OF THE PHOTOGRAPHS

The accompanying colored photographs illustrate the overall appearance of the new *Guzmania,* showing the colors as true as it is reasonably possible to obtain in colored reproductions of this type. Colors in the photographs may differ slightly from the color values cited in the detailed botanical description which accurately describe the colors of the new *Guzmania.*

The photograph on the first comprises a side perspective view of a typical flowering plant of 'Holiday' grown in a container.

The photograph on the second sheet is a close-up view of a typical inflorescence of 'Holiday'.

DETAILED BOTANICAL DESCRIPTION

All color references are measured against The Royal Horticultural Society Colour Chart, 1995 Edition. Colors and numerical measurements are approximate as plant growth and development depends on environmental conditions and cultural practices such as light level and temperature, among others, without, however any variance in genotype.

Plants used for the aforementioned photographs and the following description were about 12 months old and grown in 12-cm containers in Lithia, Fla., in a polyethylene-covered greenhouse with day temperatures ranging from 24 to 35° C., night temperatures ranging from 18 to 24° C. and light levels about 1,500 foot-candles.

Botanical classification: *Guzmania* sp. cultivar Holiday.

Parentage:

*Female, or seed, parent.*—*Guzmania* sp. cultivar Ultra (U.S. Plant Pat. No. 8,221 and U.S. Pat. No. 5,453, 563).

*Male, or pollen, parent.*—*Guzmania lingulata* cultivar El Cope, not patented.

Propagation:

*Type.*—By tissue culture.

*Time to initiate roots on tissue-cultured plants.*—Summer: About two weeks at temperatures of 26° C. Winter: About three weeks at temperatures of 21° C.

*Time to produce a rooted tissue-cultured plant.*—Summer: About 15 weeks at 26° C. Winter: About 18 weeks at 21° C.

*Root description.*—Fine, wiry, fibrous; moderate branching; initially greenish white becoming brown in color.

Plant description:

*General appearance.*—Compact, upright and outwardly arching plant habit. Closely layered strap-like leaves arranged in a basal rosette. Appropriate for 10 to 12-cm containers.

*Plant height, soil surface to top of inflorescence.*—About 24 to 27 cm.

*Plant diameter or spread.*—About 55 to 62 cm.

*Foliage description.*—Arrangement: Basal rosette, spiral phyllotaxis; sessile. Quantity of leaves per plant: Plants typically produce about 28 leaves prior to inflorescence development. Shape: Ligulate. Apex: Acute. Margin: Entire. Length: About 40 to 50 cm. Width (flattened): About 2.5 to 3 cm; width at base, about 5.7 cm. Aspect: Blade, channeled; leaves curved outward over their length and downward towards the apex. Texture, upper and lower surfaces: Leathery, stiff; glabrous. Venation: Parallel. Leaf sheath: Not observed. Color: Developing and fully expanded leaves, upper surface: Darker than, but closest to 137A; striations towards the base, 187C. Developing and fully expanded leaves, lower surface: 147B; striations towards the base 187C. Venation, upper and lower surfaces: Same as lamina.

Inflorescence description:

*Inflorescence form.*—Terminal inflorescences with showy primary bracts; inflorescences supported on erect and strong scapes.

*Inflorescence longevity.*—Inflorescences of the new *Guzmania* are very long-lasting; bract coloration is maintained for about two to three months. Inflorescences persistent.

*Natural flowering season and time to flower.*—Plants flower throughout the year and begin to flower about 13 to 16 weeks after floral induction.

*Flowers.*—Arrangement: Single flowers at the terminal of the inflorescence; one flower per terminal bract. Quantity per flower spike: About 150 flowers and flower buds. Corolla: Arrangement: Three petals, gameopetalous. Length: About 4 cm. Width: About 4 mm. Color: 155D. Calyx: Arrangement: Three petals, gameosepalous. Length: About 2.5 cm. Width: About 5 mm. Color: 155B. Reproductive organs: Stamens: Quantity per flower: Six. Filament length: About 2.9 cm. Anther length: About 5 mm. Anther color: 150D. Pistils: Style length: About 3.4 cm. Style color: 155D. Ovary: Superior with three locules. Length: About 1 cm. Color: 145D.

*Bracts.*—Quantity per flower spike, terminal bracts: About 175. Quantity per flower spike, primary bracts: About 12. Quantity per flower spike, scape bracts: About 14. Shape, terminal bracts: Ovate in shape becoming narrower and more strap-like towards the apex of the inflorescence; apices, bluntly rounded; margins, entire. Shape, primary bracts: Ovate; apices, acuminate to cuspidate; margins, entire. Primary bracts are arranged in closely-spaced vertical ranks along the inflorescence. Shape, scape bracts: Lanceolate; apices, acute; margins, entire. Scape bracts are arranged in 1.5 cm-spaced vertical ranks along the inflorescence. Length, terminal bracts: About 5.5 cm. Length, primary bracts: About 7 to 10.2 cm. Length, scape bracts: About 12 to 22 cm. Width, terminal bracts: About 1.5 cm. Width, primary bracts: About 2 to 2.5 cm. Width, scape bracts: About 2.9 cm. Texture, all bracts, upper and lower surfaces: Leathery; smooth. Color: Terminal bracts, upper and lower surfaces: 187C to 187D; apices, 155D; towards the base, 157D. Primary bracts, upper and lower surfaces: 187B; apices, 187A; towards the base, 157D. Scape bracts, upper and lower surfaces: 187C; lower scape bracts, similar in coloration and appearance to the leaves.

*Scape.*—Strength: Strong. Aspect: Typically erect. Length: About 23 cm. Diameter: About 1 cm. Texture: Smooth. Color: 154D.

*Seed/fruit.*—Seed and fruit production has not been observed.

Temperature tolerance: Plants of the new *Guzmania* have been observed to tolerate temperatures from about 4 to 40° C.

Disease/pest resistance: Plants of the new *Guzmania* have not been observed to resistant to pathogens and pests common to *Guzmania.*

It is claimed:

1. A new and distinct cultivar of *Guzmania* plant named 'Holiday', as illustrated and described.

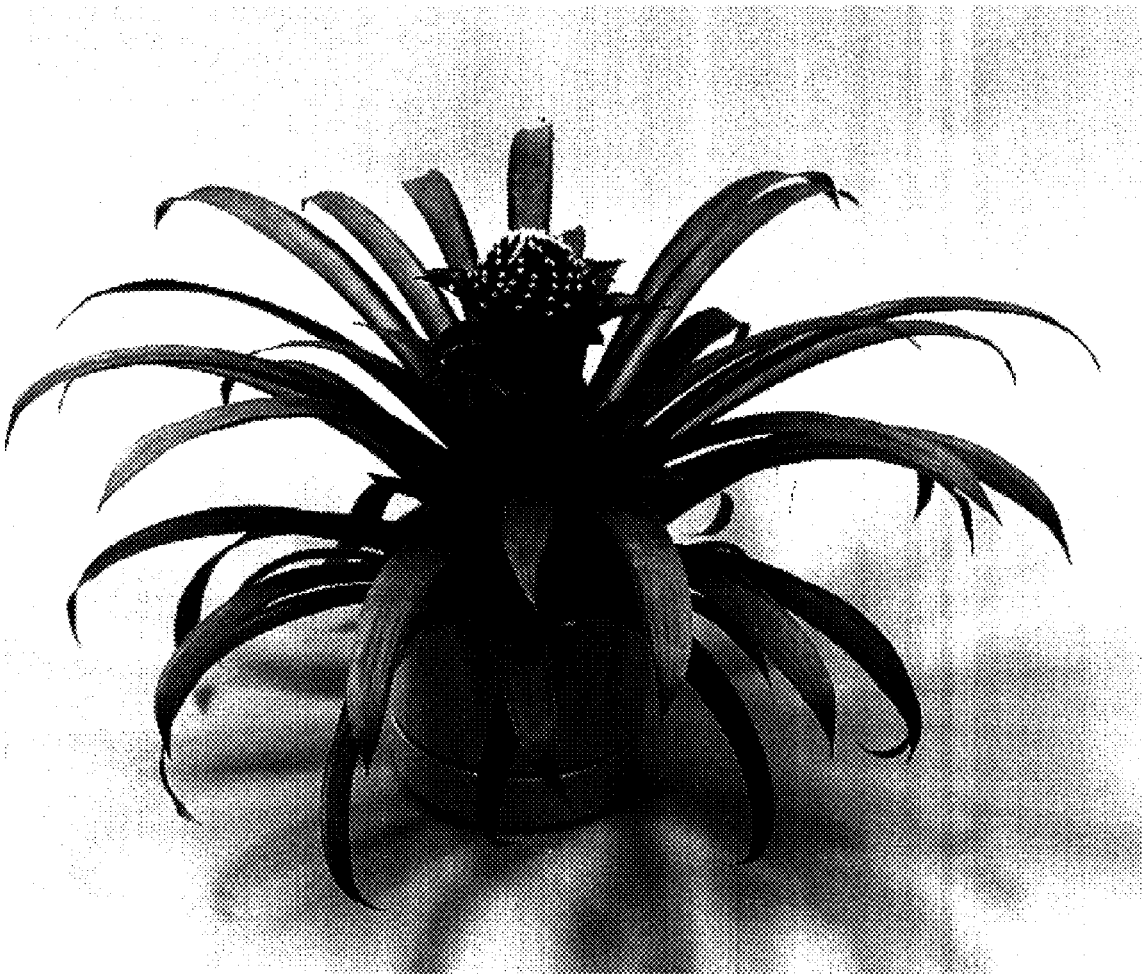

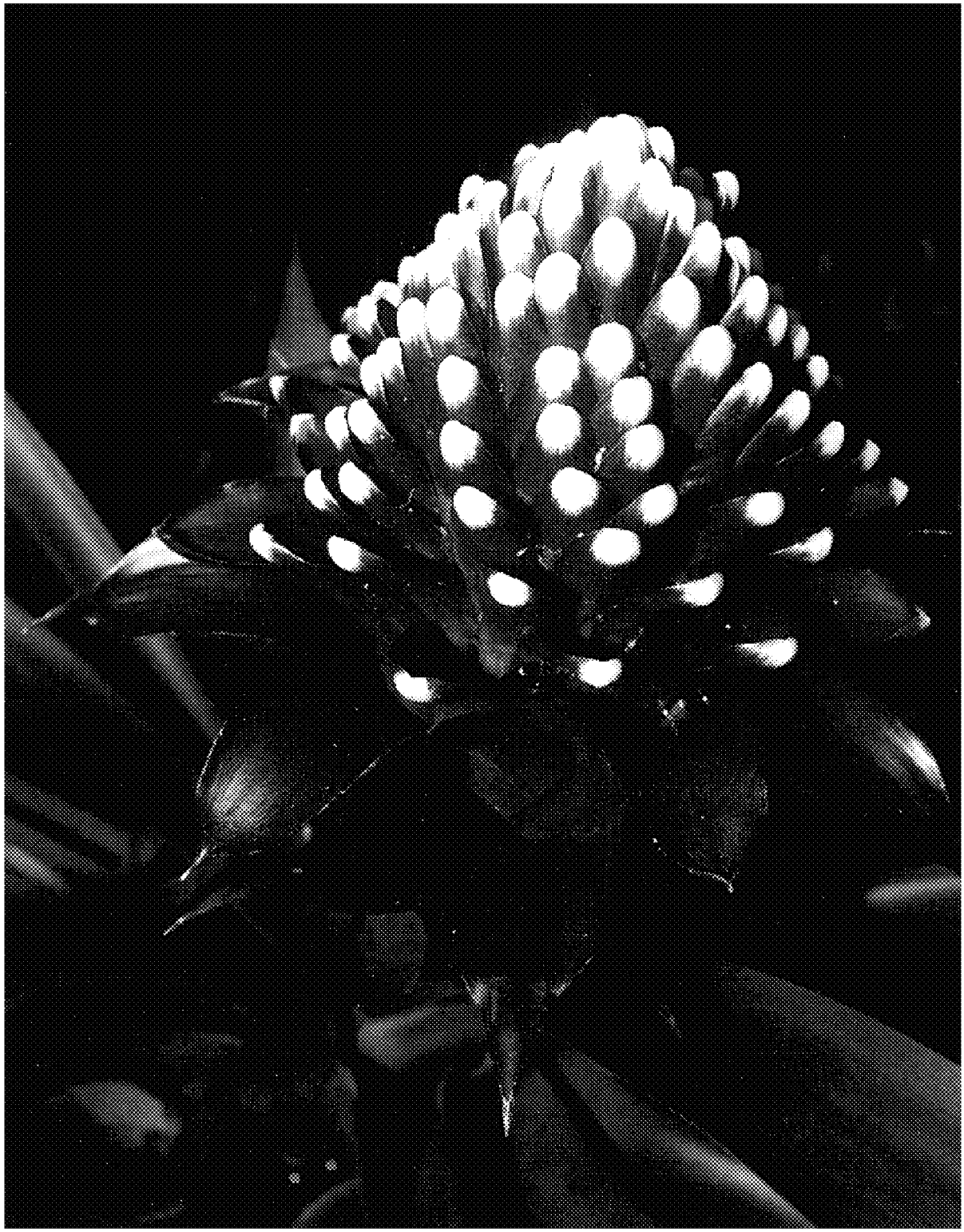

* * * * *